March 26, 1957 E. S. BOERNER Plant Pat. 1,585
ROSE PLANT
Filed July 24, 1956
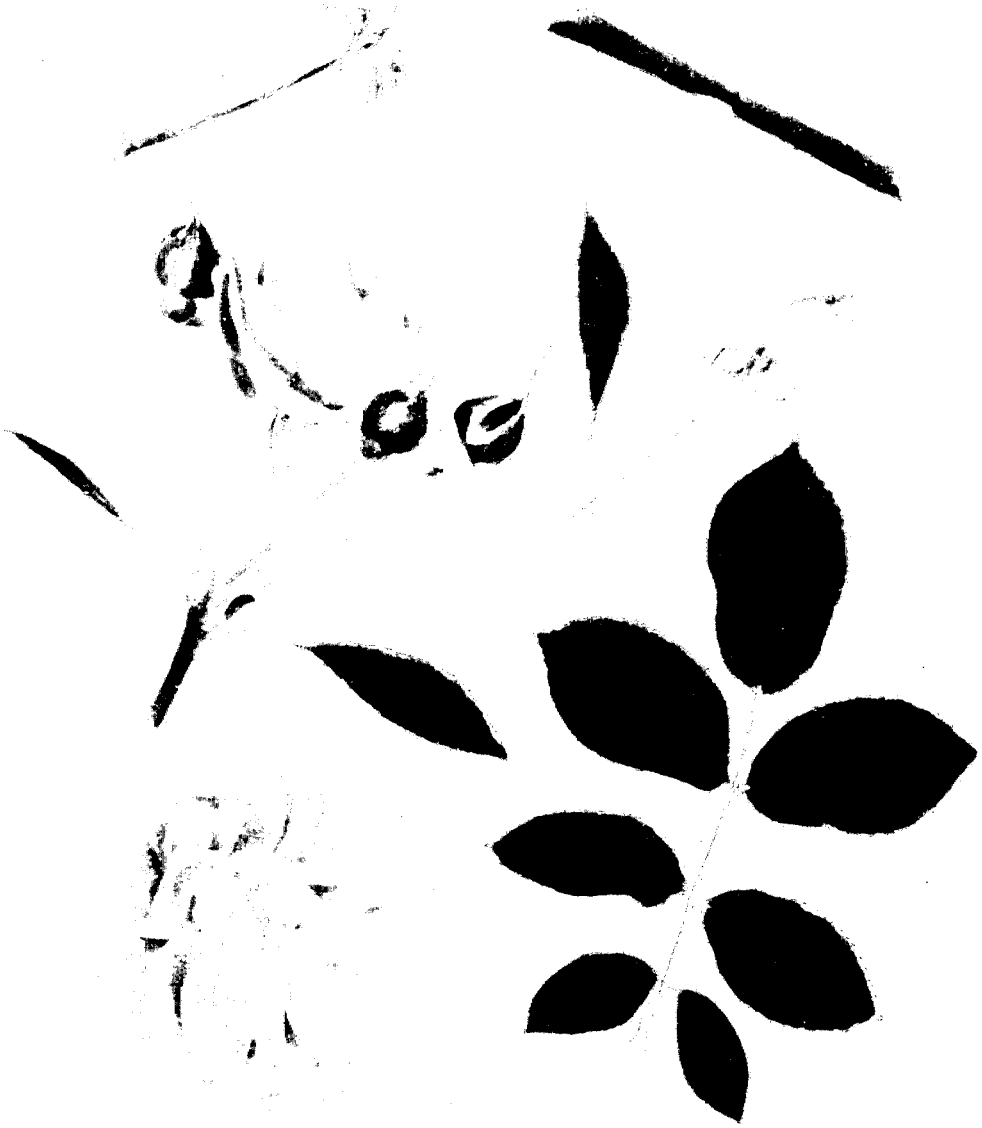
Inventor.
E. S. Boerner
By: Robb & Robb
Attorneys.

United States Patent Office

Plant Pat. 1,585

Patented Mar. 26, 1957

1,585

ROSE PLANT

Eugene S. Boerner, Newark, N. Y., assignor to Jackson & Perkins Company, Newark, N. Y., a corporation of New York Application July 24, 1956, Serial No. 599,890

1 Claim. (Cl. 47—61)

The present invention relates to a new and distinct variety of rose plant of the large-flowered polyantha class, which was originated by me by crossing an unnamed and unpatented seedling of "Lavender Pinocchio" (Plant Patent No. 947) with the patented variety "Lavender Pinocchio."

The primary objective of this cross was to produce a new rose variety having flowers of lavender shade, but which is more suitable for both outdoor and greenhouse culture. This objective was fully achieved, as evidenced by the following features which are outstanding in the new variety and which distinguish it from its parents, as well as from all other varieties of which I am aware:

(1) The symmetrical form of the plant;

(2) Its suitability for both outdoor and greenhouse culture;

(3) Its dark green foliage which achieves an uniquely attractive combination with the lavender general color tonality of its flowers; and (4) The distinctive Hellebore Red general color tonality of its half-open flowers, and the distinctive Persian Lilac, lightly overcast with Laelia Pink, general color tonality of its fully open flowers.

Asexual reproduction of my new variety by budding, as performed at Newark, New York and at Pleasanton, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.

*Seed parent.*—An unnamed seedling of "Lavender Pinocchio."

*Pollen parent.*—"Lavender Pinocchio."

Classification:

*Botanic.*—Large-flowered polyantha.

*Commercial.*—Floribunda.

*Flower*

(Observations made from specimens grown outdoors at Newark, New York in early September and at about mid-afternoon.)

Blooming habit: Recurrent—continuous.

Bud:

*Size.*—Large.

*Form.*—Globular; is not affected by wet or hot weather.

*Color.*—When sepals first divide—Indian Lake, Plate 26. When petals begin to unfurl — Rosolane Purple, Plate 26. When half-blown: inside of petals — Hellebore Red, Plate 38; reverse of petals—Hellebore Red, Plate 38, lightly overcast with Daphne Pink, Plate 38.

*Sepals.*—Slightly branched; curl back when petals begin to unfurl. Color: inside—Pale Olivine, Plate 32; outside—Light Bice Green, Plate 17.

*Calyx.* — Color — Light Bice Green, Plate 17. Shape — pear. Size — small. Aspect — smooth. Odor when rubbed—none.

*Peduncle.* — Length — short. Aspect — rough. Strength—erect; slender. Color—Absinthe Green, Plate 31.

*Opening.*—Opens up well; is not affected by adverse weather conditions.

Bloom:

*Size.*—Medium. Average size when fully expanded—3 inches.

*Borne.*—Several together and in pyramidal clusters.

*Stems.*—Medium length; normal strength.

*Form (when first open).*—Cupped. Permanence—flattens; outer petals curl back.

*Petalage.*—Double (full but open center). Number of petals under normal conditions—70.

*Color.*—Center of flower—Hellebore Red, Plate 38, lightly overcast with Daphne Pink, Plate 38. Outer petals—Pale Laelia Pink, Plate 38, lightly overcast with Laelia Pink, Plate 38. Base of petals (aiglet)—Citron Yellow, Plate 16. Inside of petals—Persian Lilac, Plate 38, lightly overcast with Laelia Pink, Plate 38. Reverse of petals—Pale Laelia Pink, Plate 38, lightly overcast with Light Pinkish Lilac, Plate 37. General tonality from a distance—Laelia Pink, Plate 38.

*Discoloration.*—General tonality at end of first day—Laelia Pink, Plate 38. Second day—Persian Lilac, Plate 38, lightly overcast with Laelia Pink, Plate 38. Third day—Laelia Pink, Plate 38, lightly overcast with Pale Laelia Pink, Plate 38.

Petals:

*Texture.*—Thick; is not affected by wet or hot weather.

*Appearance.*—Inside satiny. Outside—shiny.

*Form.*—Oval; some petals are slightly pointed.

*Arrangement.* — Imbricated (regularly arranged shingle-like).

*Petaloids in center.*—Few; small.

*Persistance.*—Drop off cleanly.

*Fragrance.*—Moderate. Nature—tea (average hybrid tea scent).

*Lasting quality.*—On the plant—very long. As cut flower—very long.

*Genital Organs*

Stamens, anthers: Small; many; mixed with Petaloids. Color—Light Cadmium, Plate 4.

Stamens, filaments (threads): Medium length. Color—Pinard Yellow, Plate 4.

Pollen: Color—Maize Yellow, Plate 4.

Styles: Columnar; uneven length; medium length; thin.

Stigmas: Color—Martius Yellow, Plate 4.

Ovaries: All enclosed in calyx.

Hips: None.

Seeds: None.

*Plant*

Form: Bush.

Growth: Upright; bushy; symmetrical.

Foliage: Compound of 5 to 7 leaflets.

*Size.*—Medium.

*Quantity.*—Abundant.

*Color.*—New foliage: upper side—Oxblood Red, Plate 1; under side—Bordeau, Plate 12, with center rib of leaf Light Cress Green, Plate 31. Old foliage: upper side—Dark Cress Green, Plate 31; under side—Light Cress Green, Plate 31.

*Shape.*—Oval pointed.

*Texture.*—Upper side—glossy. Under side—smooth.

*Ribs and veins.*—Ordinary.

*Edge.*—Serrated (saw-toothed).

*Serration.*—Single; small.

*Leaf stem.*—Color—Rainette Green, Plate 31. Under side—prickly.

*Stipules.*—Short; slightly bearded.

Wood:

*New wood.*—Color—Chromium Green, Plate 32. Bark—smooth.

*Old wood.*—Color—Deep Dull Yellow-Green, Plate 32. Bark—smooth.

Thorns:

*Thorns.*—Quantity: on main stalks from base—ordinary; on laterals from stalk—ordinary. Form—flat base; medium length; hooked downward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the symmetrical form of its plant, its suitability for both outdoor and greenhouse culture, its dark green foliage which achieves an uniquely attractive combination with the lavender general color tonality of its flowers, the distinctive Hellebore Red general color tonality of its half-open flowers and the distinctive Persian Lilac lightly overcast with Laelia Pink general color tonality of its fully open flowers.

No references cited.